United States Patent
Sugai et al.

(10) Patent No.: US 10,143,667 B2
(45) Date of Patent: Dec. 4, 2018

(54) CERAMIDE-LIKE FUNCTION IMPARTING AGENT

(71) Applicant: KAO CORPORATION, Tokyo (JP)

(72) Inventors: Yoshiya Sugai, Utsunomiya (JP); Taisuke Aosaki, Kita-ku (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/775,043

(22) PCT Filed: Mar. 11, 2014

(86) PCT No.: PCT/JP2014/056320
§ 371 (c)(1),
(2) Date: Sep. 11, 2015

(87) PCT Pub. No.: WO2014/142116
PCT Pub. Date: Sep. 18, 2014

(65) Prior Publication Data
US 2016/0038443 A1 Feb. 11, 2016

(30) Foreign Application Priority Data
Mar. 12, 2013 (JP) ................................. 2013-049331

(51) Int. Cl.
| A61K 31/164 | (2006.01) |
|---|---|
| A61K 8/42 | (2006.01) |
| A61Q 19/00 | (2006.01) |
| C07C 233/20 | (2006.01) |
| A61K 9/00 | (2006.01) |
| A61Q 17/00 | (2006.01) |

(52) U.S. Cl.
CPC .............. *A61K 31/164* (2013.01); *A61K 8/42* (2013.01); *A61K 9/0014* (2013.01); *A61Q 17/00* (2013.01); *A61Q 19/00* (2013.01); *C07C 233/20* (2013.01)

(58) Field of Classification Search
None
See application file for complete search history.

(56) References Cited

U.S. PATENT DOCUMENTS

| 3,707,511 A | 12/1972 | Lamberti et al. |
|---|---|---|
| 4,505,832 A | 3/1985 | Whiteman et al. |
| 4,778,823 A | 10/1988 | Kawamata et al. |
| 5,541,341 A | 7/1996 | Vermeer et al. |
| 5,631,389 A | 5/1997 | Vermeer et al. |
| 2004/0115162 A1 | 6/2004 | Hoshino et al. |

FOREIGN PATENT DOCUMENTS

| CZ | 289 465 | 1/2002 |
|---|---|---|
| JP | 62 228048 | 10/1987 |
| JP | 9 509668 | 9/1997 |
| JP | 10-510287 A | 10/1998 |
| JP | 2002 47261 | 2/2002 |
| WO | WO 96/16930 A1 | 6/1996 |
| WO | 00 61097 | 10/2000 |

OTHER PUBLICATIONS

Wu (https://www.everydayhealth.com/hs/dry-skin-relief/dr-wu-causes-of-dry-skin/, obtained from the internet on Jan. 17, 2018, last updated Sep. 20, 2010).*
Cambridge Dictionary Online (https://dictionary.cambridge.org/us/dictionary/english/thereby, obtained from the internet on Jan. 17, 2018).*
Extended European Search Report dated Aug. 22, 2016 in Patent Application No. 14764366.2.
Database CA [Online] Chemical Abstracts Service, Columbus, Ohio, US, Sep. 13, 2012, Hamada Naohiro et al., "beta-hydroxyalkyl amide and photosensitive resin composition", XP002760666 retrieved from STN Database Accesion No. 2012:1335566 & Database Registry [Online] Chemical Abstracts Service, Columbus, Ohio, US; Oct. 3, 2012 "Butanediamide, 2-dodecyl-N1, N4-bis [1-(hydroxymethyl) butyl]—", XP002760667, Database Accesion No. 1398509-09-5.

(Continued)

*Primary Examiner* — Marcos L Sznaidman
*Assistant Examiner* — Rayna Rodriguez
(74) *Attorney, Agent, or Firm* — Oblon, McClelland, Maier & Neustadt, L.L.P.

(57) ABSTRACT

Provided are an agent for imparting ceramide-like function, an agent for reinforcing skin barrier function, a moisturizing agent and a skin drug for external use.
The agent for imparting ceramide-like function comprises as an effective ingredient a derivative of succinic acid diamide represented by the following formula (1):

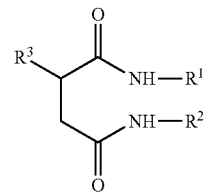

(1)

[wherein $R^1$ and $R^2$ each independently represents a hydroxyalkyl group of from 1 to 6 carbon atoms, $R^3$ represents a group: $-CH_2CH_2CH_2CH_2-R^4$ or a group: $-CH_2CH=CHCH_2-R^4$ (wherein $R^4$ represents an alkyl group of from 8 to 26 carbon atoms)].

28 Claims, No Drawings

(56) References Cited

OTHER PUBLICATIONS

International Search Report dated Jun. 3, 2014 in PCT/JP2014/056320 filed Mar. 11, 2014.
International Preliminary Report on Patentability and Written Opinion dated Sep. 24, 2015 in PCT Application No. PCT/JP2014/056320.

* cited by examiner

CERAMIDE-LIKE FUNCTION IMPARTING AGENT

CROSS REFERENCE TO RELATED APPLICATION

This application is a 371 of PCT/JP2014/056320, filed on Mar. 11, 2014, and claims priority to Japanese Patent Application 2013-049331, filed on Mar. 12, 2013.

FIELD OF THE INVENTION

The present invention relates to an agent for imparting ceramide-like function, an agent for reinforcing skin barrier function, a moisturizing agent and a skin drug for external use, all using a compound having ceramide-like functions.

BACKGROUND OF THE INVENTION

Ceramides, one of sphingolipids, are lipids contained in very small amount in the whole body of living organism, but they account for at least half of the intercellular lipids in the horny cell layer that is the outermost layer of skin layers, and they play an important role in the skin's barrier mechanism. The ceramides function after they were produced and secreted in epidermal cells to constitute an intercellular lamellar structure in a horny cell layer.

However, as to skin diseases such as dry skin, irritated skin, atopic dermatitis, senile xerosis and psoriasis, there have been many reports that healthy metabolism of ceramides is disturbed and ceramides content in horny cell layer is decreased, thereby causing the decrease in the skin's moisturizing function and barrier function.

For treating such skin diseases, a method of supplementing externally natural ceramides of animal or plant origin and of microorganism origin, chemically synthesized ceramides and/or ceramide analogues has been investigated. However, due to small amount of ceramides contained in each individual of animals, plants and microorganisms, ceramides are difficult to isolate and expensive. Certain types of ceramides having a specified structure are industrially produced through chemical synthesis. However, the production involves problems with respect to the function of the ceramide produced and expensive production cost. On the other hand, ceramide analogues having functions similar to those of ceramides have been studied and reported (e.g., Patent Document 1, etc.), but their effects were not necessarily satisfactory.

Meanwhile, it has been known that certain compounds of alkyl succinic acid diamide exhibit a surfactant effect and the like (Patent Document 2).

It has not been known, however, that a specific derivative of succinic acid diamide shows a ceramide-like effect.

CITATION LIST

Patent Documents

Patent Document 1: JP 62-228048 A
Patent Document 2: U.S. Pat. No. 5,541,341 A

SUMMARY OF THE INVENTION

The present invention is directed to the following 1) to 16).

1) An agent for imparting ceramide-like functions, comprising as an active ingredient a derivative of succinic acid diamide represented by the following formula (1).

2) An agent for reinforcing skin barrier function, comprising as an active ingredient a derivative of succinic acid diamide represented by the following formula (1).

3) A moisturizing agent comprising as an active ingredient a derivative of succinic acid diamide represented by the following formula (1).

4) A skin drug for external use comprising a derivative of succinic acid diamide represented by the following formula (1).

5) Use of a derivative of succinic acid diamide represented by the following formula (1) for production of an agent for imparting ceramide-like functions.

6) Use of a derivative of succinic acid diamide represented by the following formula (1) for production of an agent for reinforcing skin barrier function.

7) Use of a derivative of succinic acid diamide represented by the following formula (1) for production of a moisturizing agent.

8) Use of a derivative of succinic acid diamide represented by the following formula (1) for production of a skin drug for external use.

9) A derivative of succinic acid diamide represented by the following formula (1) for use of imparting ceramide-like functions.

10) A derivative of succinic acid diamide represented by the following formula (1) for use of reinforcing skin barrier function.

11) A derivative of succinic acid diamide represented by the following formula (1) for use of skin moisturizing.

12) A derivative of succinic acid diamide represented by the following formula (1) for external use on the skin.

13) A method for imparting ceramide-like function, comprising administering a derivative of succinic acid diamide represented by the following formula (1).

14) A method for reinforcing skin barrier function, comprising administering a derivative of succinic acid diamide represented by the following formula (1).

15) A method for moisturizing skin, comprising administering a derivative of succinic acid diamide represented by the following formula (1).

16) A derivative of succinic acid diamide represented by the following formula (2):

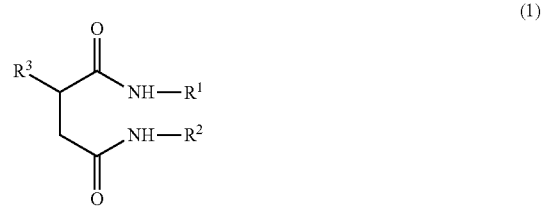

[wherein, $R^1$ and $R^2$ each independently represents a hydroxyalkyl group of from 1 to 6 carbon atoms, $R^3$ represents a group: $-CH_2CH_2CH_2CH_2-R^4$ or a group: $-CH_2CH=CHCH_2-R^4$ (wherein $R^4$ represents an alkyl group of from 8 to 26 carbon atoms)].

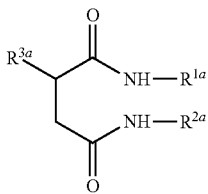

(2)

[wherein $R^{1a}$ and $R^{2a}$ represent a 2-hydroxyethyl group, $R^{3a}$ represents a group: —$CH_2CH_2CH_2CH_2$—$R^{4a}$ or a group: —$CH_2CH$=$CHCH_2$—$R^{4a}$ (wherein $R^{4a}$ represents an alkyl group of from 12 to 26 carbon atoms].

DETAILED DESCRIPTION OF THE INVENTION

The present invention relates to providing an agent for imparting ceramide-like function which provides a function similar to that of ceramides, an agent for reinforcing skin barrier function, a moisturizing agent and a skin drug for external use.

The present inventors conducted extensive studies on chemically synthesized ceramide-like compounds, and as a result, found that a derivative of succinic acid diamide represented by the following formula (1) has a stable lamellar-forming ability similar to natural ceramides, an excellent transepidermal water loss (TEWL)-inhibiting effect and a water retaining effect, and thus is useful as a compound which may provide ceramide-like functions.

Since the derivatives of succinic acid diamide according to the invention have functions similar to those of natural ceramides, they can be used as an agent for imparting ceramide-like functions, an agent for reinforcing skin barrier function, a moisturizing agent, or a skin drug for external use. By applying these agents to the human body, TEWL is inhibited to retain water, whereby enabling improvement of dry skin, etc. to maintain the skin in a healthy condition.

In formula (1), the alkyl group in the hydroxyalkyl group of from 1 to 6 carbon atoms represented by $R^1$ and $R^2$ may be either a linear or branched chain, and preferably contains 2 or more to 4 or less carbon atoms. The number of the hydroxyl group contained therein is 1 or more to 5 or less, preferably 4 or less, more preferably 2 or less.

Specifically, examples of the hydroxyalkyl group include, for example, 2-hydroxyethyl group, 3-hydroxypropyl group, 1-hydroxypropan-2-yl group, 4-hydroxybutyl group, 1,3-dihydroxy-2-methylpropan-2-yl group, 1,3-dihydroxy-2-(hydroxymethyl)propan-2-yl group, 1,2-dihydroxypropan-3-yl group, 1-hydroxy-2-(hydroxymethyl)propan-3-yl group, 1,3-dihydroxy-2-ethylpropan-2-yl group, 1,2,3,4,5-pentahydroxyhexan-6-yl group, etc.

Among them, preferred are 2-hydroxyethyl group, 3-hydroxypropyl group, 1-hydroxypropan-2-yl group, 1,3-dihydroxy-2-methylpropan-2-yl group and 1,3-dihydroxy-2-(hydroxymethyl)propan-2-yl group, and more preferred is 2-hydroxyethyl group.

Such $R^1$ and $R^2$ may be identical or different, but are preferably the same hydroxyalkyl group of from 1 to 6 carbon atoms, for example, both of them are a 2-hydroxyethyl group.

In the group: —$CH_2CH_2CH_2CH_2$—$R^4$ or the group: —$CH_2CH$=$CHCH_2$—$R^4$ represented by $R^3$, the alkyl group of from 8 to 26 carbon atoms represented by $R^4$ may have either a linear chain or a branched chain, but preferably is a linear alkyl group, and the number of the carbon atoms thereof is preferably 8 or more, more preferably 12 or more, and is preferably 22 or less, more preferably 20 or less. An example of the number of the carbon atoms is from 8 to 22 or from 12 to 20.

Specific examples of the alkyl group $R^4$ include octyl group, nonyl group, decyl group, undecyl group, dodecyl group, tridecyl group, tetradecyl group, pentadecyl group, hexadecyl group, heptadecyl group, octadecyl group, nonadecyl group, icosyl group, docosyl group, tricosyl group, tetracosyl group, pentacosyl group, hexacosyl group, 2-ethylhexyl group, 2-hexyldecyl group, 2-octylundecyl group, 2-decyltetradecyl group and the like. Among them, preferred are dodecyl group, tetradecyl group, hexadecyl group, octadecyl group and icosyl group, and more preferred are hexadecyl group, octadecyl group and icosyl group.

Further, in the derivative of succinic acid diamide represented by formula (1) according to the invention, they may exist as an isomer such as an optical isomer, e.g., a d-form isomer or an l-form isomer, or a rotational isomer, depending on the kind of substituent and a combination thereof. Both of mixtures of these isomers and isolated isomers are included in the present invention.

In the ceramide-like function-imparting agent, barrier function-reinforcing agent and moisturizing agent according to the invention, the derivative of succinic acid diamide represented by formula (1) can be a single compound or a mixture of two or more compounds. Examples of such mixtures include a mixture of plural compounds in which $R^4$ in the group —$CH_2CH_2CH_2CH_2$—$R^4$ or —$CH_2CH$=$CHCH_2$—$R^4$ represented by $R^3$ has carbon atoms in the range of from 12 to 20 or from 16 to 20.

Among the derivatives of succinic acid diamide represented by formula (1) according to the invention, preferred in view of ceramide-like functions are a compound in which both of $R^1$ and $R^2$ are a hydroxyalkyl group of from 1 to 6 carbon atoms; a compound in which both of $R^1$ and $R^2$ are a 2-hydroxyethyl group; a compound in which both of $R^1$ and $R^2$ are a hydroxyalkyl group of from 1 to 6 carbon atoms and $R^3$ is a group —$CH_2CH$=$CHCH_2$—$R^4$; a compound in which both of $R^1$ and $R^2$ are a 2-hydroxyethyl group and $R^3$ is a group —$CH_2CH$=$CHCH_2$—$R^4$; a mixture of plural compounds in which $R^4$ in the group —$CH_2CH$=$CHCH_2$—$R^4$ represented by $R^3$ has carbon atoms in the range of from 12 to 20; and a mixture of plural compounds in which $R^4$ in the group —$CH_2CH$=$CHCH_2$—$R^4$ represented by $R^3$ has carbon atoms in the range of from 16 to 20.

Among the derivatives of succinic acid diamide represented by formula (1) according to the invention, novel compounds not described in literature are such compounds (of formula (2)) in which both of $R^1$ and $R^2$ are a 2-hydroxyethyl group, $R^3$ is a group —$CH_2CH$=$CHCH_2$—$R^4$ and $R^4$ has carbon atoms in the range of from 12 to 26.

The derivatives of succinic acid diamide represented by formula (1) according to the invention can be prepared by using an amidation reaction and a reduction reaction both of which are known.

The compound wherein $R^1$ and $R^2$ represent the same group can be prepared, as shown, for example, by the following <Reaction scheme 1>, by condensing an alkenyl succinic anhydride (A) or a diester of alkenyl succinic acid (B) with an amine compound (C) (Process-1 or Process-1'), and the compound wherein $R^3$ represents an alkyl group (group: —$CH_2CH_2CH_2CH_2$—$R^4$) can be prepared by subjecting the resultant compound to a reduction reaction (Process-2).

In the above, the reaction in the Process-1 can be conducted by stirring in the presence or absence of a solvent at a temperature in the range of, for example, from 0 to 180° C., for 10 minutes to 24 hours. Incidentally, when a solvent is used, as the solvent can be used, for example, dimethylsulfoxide, xylene, toluene, dioxane, etc.

The reaction in the Process-1' can be conducted by stirring in the presence of a base such as sodium methoxide, sodium ethoxide or tert-butoxypotassium in a suitable solvent (such as dichloromethane, chloroform, tetrahydrofuran, dioxane, ethanol or methanol) at a temperature in the range of, for example, from 0 to 150° C., for 10 minutes to 24 hours.

The reduction reaction in the Process-2 is preferably a catalytic reduction. In this case, examples of preferred catalyst include a palladium-activated carbon, a platinum oxide, etc. Examples of preferred solvent include ethanol, methanol, tetrahydrofuran, ethyl acetate, etc.

The compound wherein $R^1$ and $R^2$ represent different groups can be prepared, as shown, for example, by the following <Reaction scheme 2>, by reacting an alkenyl succinic anhydride (A) with an amine compound (D) to give a pyrrolidinedione compound (E)(Process-3), and condensing the resultant compound with an amine compound (F) (Process-4). The compound wherein $R^3$ represents an alkyl group can be prepared by further subjecting the resultant compound to a reduction process (Process-5).

The reaction in the Process-3 can be conducted by stirring in the presence or absence of a base such as sodium methoxide, sodium ethoxide or tert-butoxypotassium at a temperature in the range of, for example, from 0 to 180° C., for 10 minutes to 24 hours.

Process-4 and Process-5 can be conducted in a manner similar to Process-1 and Process-2, respectively.

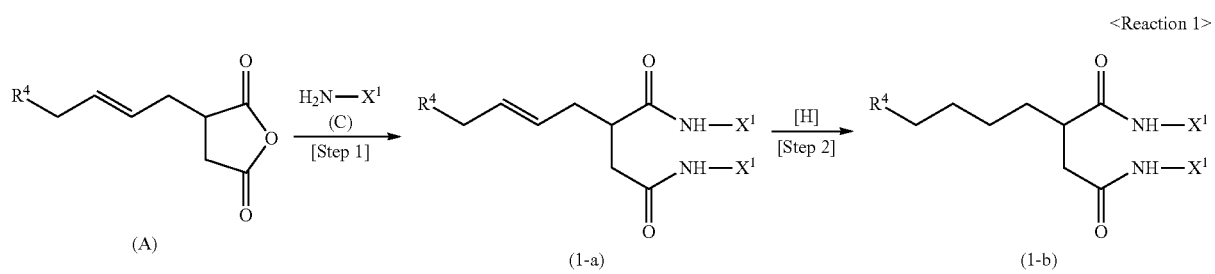

<Reaction 1>

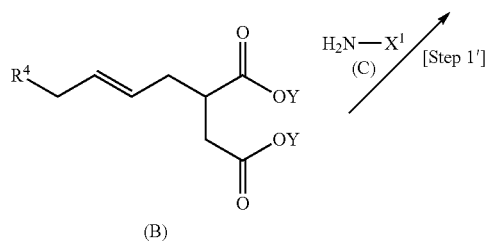

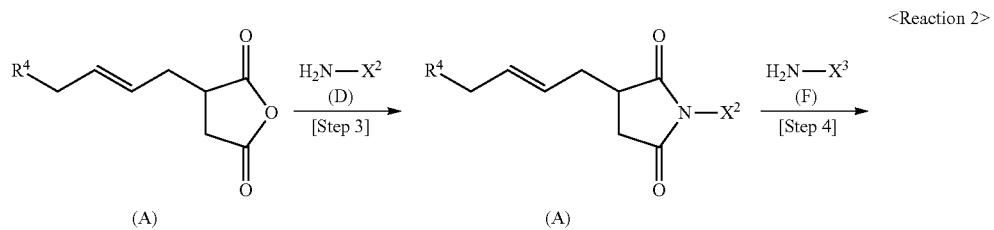

<Reaction 2>

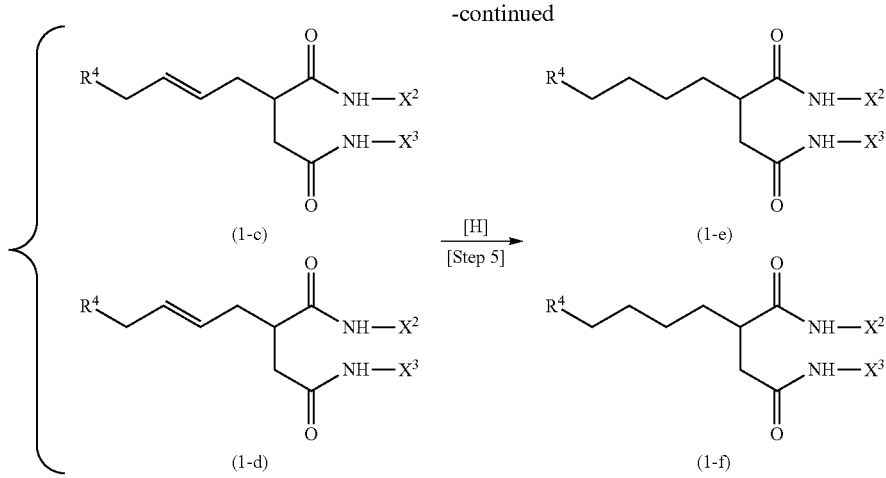

[wherein Y represents a lower alkyl group (ethyl group, methyl group, etc.), $R^4$ represents the same group as defined above, and each of $X^1$, $X^2$ and $X^3$ represents the group as defined above for $R^1$ or $R^2$].

Any of the alkenyl succinic anhydrides (A) used as a raw material is a known compound and can be prepared according to a known method (JP 60-78975 A A). For example, it can be prepared by stirring a mixture of an anhydrous maleic acid and a corresponding α-olefin in the presence of a polymerization inhibitor and an antioxidant at a temperature between 150° C. and 260° C. for 10 minutes to 24 hours.

Incidentally, isolation of the compound in each of the reactions may be conducted, if necessary, by a purification method conventionally used in synthetic organic chemistry, such as filtration, washing, drying, recrystallization, various chromatographies, distillation or the like.

The derivatives of succinic acid diamide represented by formula (1) of the invention need not necessarily be pure and may be crude products when used for various applications. For example, examples of the crude product include those having a purity of 80% by mass or more, 90% by mass or more, 95% by mass or more, even 98% by mass or more, or even more 99% by mass or more. For example, even if the crude product includes a reaction intermediate, i.e., a pyrrodinedione compound (E), it can develop functions as far as it has the above-mentioned purity.

The derivative of succinic acid diamide represented by formula (1) of the invention exhibits functions similar to or superior to those of ceramides (ceramide-like functions) as shown by the examples described below. Specifically, the derivative forms a lamellar structure together with intercellular lipids in a horny cell layer, and exhibits a TEWL-suppressing effect and a water-retaining effect.

Ceramides form a lamellar structure together with intercellular lipids (stearic acid, cholesterol, etc.) in a horny layer (lamellar forming ability) and have an important role in a skin moisture-retaining mechanism and a barrier mechanism (i.e., a TEWL-inhibiting mechanism) (G. Imokawa, et al., J. Invest. Dermatol., 87, 758-761 (1986)). By the lamellar forming ability herein is meant formation of a multi-lamellar structure consisting of a lipid bimembrane and a water layer like a horny layer of intercellular lipids. By the moisture-retaining mechanism is meant an effect to provide skin with flexibility by including an appropriate amount of water, thereby giving a smooth and beautiful skin. By the barrier mechanism is meant effects to prevent water from getting out of the body and keep the body not dried up, as well as to prevent external foreign matters from entering into the body.

In the present invention, by the "ceramide-like functions" is meant to retain a lamellar-forming ability, a moisture-retaining mechanism and a barrier mechanism similar to or superior to those of natural ceramides.

Accordingly, the derivative of succinic acid diamide represented by formula (1) of the invention can be an agent for imparting ceramide-like functions, a moisturizing agent and an agent for reinforcing a barrier function (abbreviated as "ceramide-like function-imparting agent and the like"), and, when applied to a human body, it can impart ceramide-like functions and reinforce a moisturizing effect and a barrier function.

In the application to the human body as described above, the application may be a therapeutic use or non-therapeutic use. The term "non-therapeutic" means a concept that excludes medical practice, namely a concept that excludes operation, treatment or diagnosis of the human body, and specifically a concept that excludes a method for operating, treating or diagnosing the human body conducted by a physician or a person instructed by a physician.

In addition, the derivative of succinic acid diamide represented by formula (1) of the invention can be used for producing a ceramide-like function-imparting agent and the like.

The ceramide-like function-imparting agent and the like may themselves be a cosmetic, a medicine or a quasi-drug for imparting and providing ceramide-like functions, improving a water-retaining ability of skin (moisture retention) and reinforcing a barrier function of skin, or, alternatively, may be a material or a preparation to be incorporated into the cosmetic, medicine, quasi-drug or the like as a skin drug for external use.

The medicine or quasi-drug may be administered in an optional dosage form. In the present invention, by the term "administration" is meant applying the derivative of succinic acid diamide represented by formula (1) to a subject via an administration route which can develop in the subject intended functions of imparting and providing ceramide-like functions, improving the water-retaining ability of skin (moisture retention) and reinforcing the barrier function of skin in an effective dose and for an effective period of time. The administration route includes a parenteral administration administered in any of the forms of, for example, injections, suppositories, inhalation drugs, transdermal drugs or external drugs, as well as an oral administration administered in any of the forms of tablets, capsule, granules, powders, syrups or the like. Among them, preferred is a parenteral administration, and more preferred is an external administration administered in the form of an external drug. The external administration herein is preferably conducted via a measure wherein a skin drug for external use (for example, in the form of ointment, emulsified cosmetic, cream, emulsion, lotion or gel), i.e., a preparation comprising the derivative of succinic acid diamide represented by formula (1), is caused to contact directly or indirectly with the whole of or a part of the skin surfaces of the human body (including skin surfaces after dehairing and also after removing horny cell layer) in an effective amount for an effective period of time (for example, from 0 to 24 hours, preferably from 3 to 24 hours) to deliver the derivative of succinic acid diamide to the epidermis and/or dermis or to a specified layer the skin. In this connection, the indirect contact includes a measure wherein the skin drug for external use is applied to a predetermined surface of an absorbent article such as diaper, sanitary napkin, panty liner or incontinence pad, i.e. a surface which contacts the skin of a wearer during wearing, whereby transferring the derivative of succinic acid diamide of formula (1) to the skin of the wearer. By this measure, the ceramide-like functions are imparted to the skin that contacts the surface applied with the drug, and irritation and redness of the skin can be inhibited. The absorbent article herein usually consists of a plural number of sheets (liquid-permeable sheets, liquid impermeable sheets) and an absorbent body, and no particular limitation is imposed on the structure thereof. The skin drug for external use (the derivative of succinic acid diamide of formula (1)) is applied to the absorbent article over the whole or a part of the surfaces where the skin of the wearer of the absorbent article comes into contact, as it is or after optionally adjusting the viscosity of the drug, by way of a coating method such as a dice coater method or a slot spraying method.

For preparing the medicine or quasi-drug, the derivative of succinic acid diamide of formula (1) can be used solely or optionally in combination with a pharmaceutically acceptable excipient, binder, bulking agent, disintegrating agent, surfactant, lubricant, dispersant, buffering agent, preserving agent, flavoring agent, fragrance, coating agent, carrier, diluting agent or the like. These medicines or quasi-drugs may be incorporated with, besides the derivative of succinic acid diamide of formula (1), plant extracts, analgesic antiphlogistic agents, analgesic agents, bactericides, astringents, skin softening agents, hormones, vitamins, humectants, anti-inflammatory agents, algefacients, antiseborrheic agents or the like as long as they do not hinder the effects of the present invention.

The content of the derivative of succinic acid diamide of formula (1) of the invention in the medicine or quasi-drug is preferably 0.001% by mass or more, more preferably 0.01% by mass or more, and preferably 10% by mass or less, more preferably 5% by mass or less, further more preferably 3% by mass or less. The content is preferably in the range of from 0.001 to 10% by mass, more preferably from 0.01 to 5% by mass, further more preferably from 0.01 to 3% by mass.

In addition, a dose per day of the medicine or quasi-drug for an adult is, for example, preferably 0.001 mg or more, more preferably 0.01 mg or more, and preferably 1000 mg or less, more preferably 500 mg or less, reduced to the amount of the derivative of succinic acid diamide of formula (1) of the invention. In addition, the dose is preferably in the range of from 0.001 to 1000 mg, more preferably from 0.01 to 500 mg.

The cosmetics may be any of skin drugs for external use, washing agents and make-up cosmetics. Depending on the method of use, the cosmetics are supplied in various forms such as beauty lotions, face lotions, massaging agents, lotions, emulsions, gels, creams, ointments, powders, packs, granules, foundations, lip sticks, bath additives, shampoos, hair conditioners, hair tonics, tablets, capsules, absorbent articles and sheet-like products.

Such cosmetics can be prepared by using the derivative of succinic acid diamide of formula (1) of the invention solely or optionally in combination with oily ingredients, humectants, powders, dyes, emulsifying agents, solubilizers, washing agents, ultraviolet absorbing agents, thickeners, medicinal ingredients, flavors, resins, bactericidal fungicidal agents, plant extracts, alcohols or the like. Incidentally, examples of the medicinal ingredients include, for example, sodium hyaluronate.

The content of the derivative of succinic acid diamide of formula (1) of the invention in the cosmetics is preferably 0.001% by mass or more, more preferably 0.01% by mass or more, and preferably 10% by mass or less, more preferably 5% by mass or less, further more preferably 3% by mass or less. The content is preferably in the range of from 0.001 to 10% by mass, more preferably from 0.01 to 5% by mass, further more preferably from 0.01 to 3% by mass.

The subject to be applied with the medicine, quasi-drug or cosmetic is not particularly limited as long as application thereof is required, but is preferably a human body which requires impartment of ceramide functions, reinforcement and soundness (returning to health) of skin barrier functions, and improvement (moisture retention) in water-retention ability (moisture retention) of skin.

In regard to the above-mentioned modes, the following embodiments are disclosed by the present invention:

<1> An agent for imparting ceramide-like function comprising as an effective ingredient a derivative of succinic acid diamide of the following formula (1).

<2> An agent for reinforcing skin barrier function comprising as an effective ingredient a derivative of succinic acid diamide of the following formula (1).

<3> A moisturizing agent comprising a derivative of succinic acid diamide of the following formula (1) as an effective ingredient.

<4> A skin drug for external use comprising a derivative of succinic acid diamide of the following formula (1) as an effective ingredient.

<5> Use of a derivative of succinic acid diamide of the following formula (1) for preparing an agent for imparting ceramide-like function.

<6> Use of a derivative of succinic acid diamide of the following formula (1) for preparing an agent for reinforcing skin barrier function.

<7> Use of a derivative of succinic acid diamide of the following formula (1) for preparing a moisturizing agent.

<8> Use of a derivative of succinic acid diamide of the following formula (1) for preparing a skin drug for external use.

<9> A derivative of succinic acid diamide of the following formula (1) for use in imparting ceramide-like function.

<10> A derivative of succinic acid diamide of the following formula (1) for use in reinforcing skin barrier function.

<11> A derivative of succinic acid diamide of the following formula (1) for use in moisturizing.

<12> A derivative of succinic acid diamide of the following formula (1) for use in external use for skin.
<13> A method for imparting ceramide-like function which comprises administering a derivative of succinic acid diamide of the following formula (1).
<14> The method for imparting ceramide-like function according to <13>, comprising administering an effective amount of the derivative of succinic acid diamide of the following formula (1) to the human body for the purpose of reinforcing and returning to health of skin barrier functions or improvement in water-retention ability of skin.
<15> The method for imparting ceramide-like function according to <14>, which comprising making the derivative of succinic acid diamide of the following formula (1) contact directly or indirectly with a skin surface of the human body to deliver an effective amount of the derivative of succinic acid diamide to the epidermis and/or dermis of the skin.
<16> The method for imparting ceramide-like function according to <14> or <15>, comprising administering from 0.001 mg to 1000 mg per day of the derivative of succinic acid diamide of the following formula (1).
<17> A method for reinforcing skin barrier function which comprises administering a derivative of succinic acid diamide of the following formula (1).
<18> A method of moisturizing, comprising administering a derivative of succinic acid diamide of the following formula (1).
<19> The derivative of succinic acid diamide according to <9> to <12>, which is for non-therapeutic use.
<20> The method according to <13> to <18>, which is non-therapeutic.
<21> In the foregoing <1> to <20>, the derivative of succinic acid diamide of formula (1) is preferably the one wherein both of $R^1$ and $R^2$ are a hydroxyalkyl group of from 1 to 6 carbon atoms.
<22> In the foregoing <1> to <20>, the derivative of succinic acid diamide of formula (1) is preferably the one wherein both of $R^1$ and $R^2$ are a 2-hydroxyethyl group.
<23> In the foregoing <1> to <22>, the content of the derivative of succinic acid diamide of formula (1) is preferably 0.001% by mass or more, more preferably 0.01% by mass or more, and preferably 10% by mass or less, more preferably 5% by mass or less, further more preferably 3% by mass or less. The content is preferably in the range of from 0.001 to 10% by mass, more preferably from 0.01 to 5% by mass, further more preferably from 0.01 to 3% by mass.
<24> A derivative of succinic acid diamide represented by the following formula (2).
<25> An absorbent article, wherein a derivative of succinic acid diamide of the following formula (1) is applied to the surface of the article which the skin of a wearer touches during use.
<26> An absorbent article, wherein a ceramide-like function-imparting agent comprising as an effective ingredient a derivative of succinic acid diamide of the following formula (1) is applied to the surface of the article which the skin of a wearer touches during use.

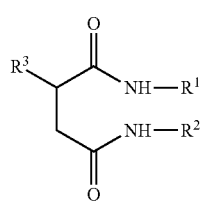
(1)

[wherein $R^1$ and $R^2$ each independently represents a hydroxyalkyl group of from 1 to 6 carbon atoms, $R^3$ represents a group: —$CH_2CH_2CH_2CH_2$—$R^4$ or a group: —$CH_2CH$=$CHCH_2$—$R^4$ (wherein $R^4$ represents an alkyl group of from 8 to 26 carbon atoms)].

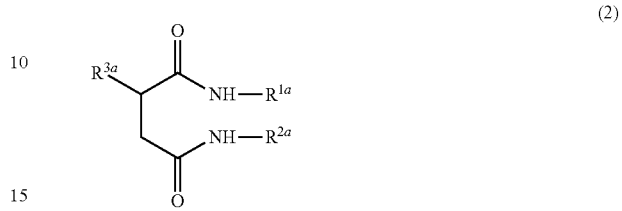
(2)

[wherein $R^{1a}$ and $R^{2a}$ represent a 2-hydroxyethyl group, $R^{3a}$ represents a group: —$CH_2CH_2CH_2CH_2$—$R^{4a}$ or a group: —$CH_2CH$=$CHCH_2$—$R^{4a}$ (wherein $R^{4a}$ represents an alkyl group of from 12 to 26 carbon atoms].

EXAMPLES

Preparation Example 1: Synthesis of (E)-2-(hexadeca/octadeca)-2-en-1-yl)-N,N,-bis(2-hydroxyethyl) succinamide (Compound 1)

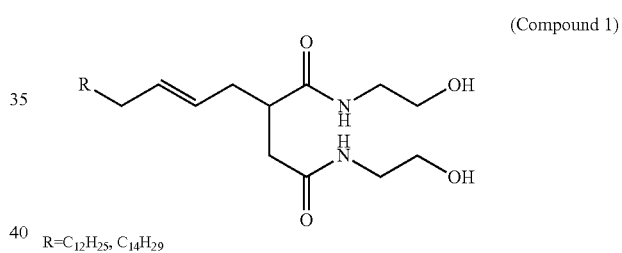
(Compound 1)

R=$C_{12}H_{25}$, $C_{14}H_{29}$

<Production scheme>

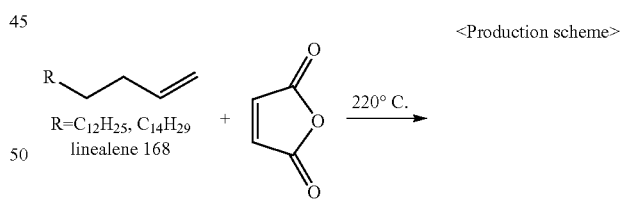

R=$C_{12}H_{25}$, $C_{14}H_{29}$
linealene 168

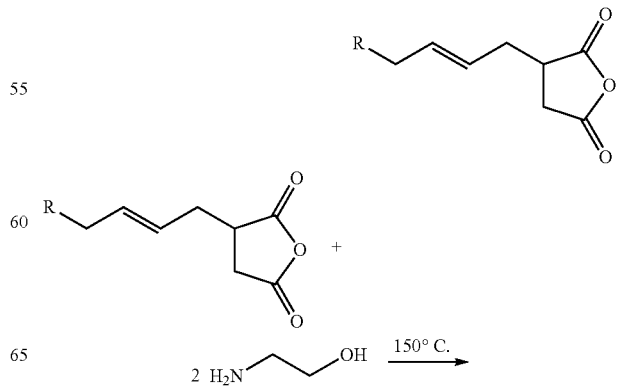

-continued

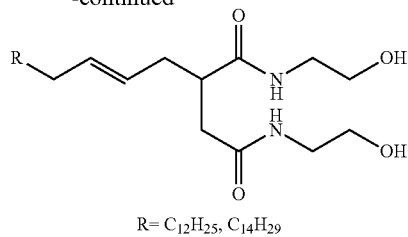

R= $C_{12}H_{25}$, $C_{14}H_{29}$

Ethanolamine (50.4 g, 0.825 mol) was heated at 150° C. with stirring under a nitrogen atmosphere, and thereto was added over one hour a molten alkenylsuccinic anhydride (mole ratio: C16/C18=6/4, synthesized from linealene 168 (IDEMITSU Kosan Co., Ltd.) and maleic anhydride) (54.5 g, 0.163 mol). After 9 hours, stirring was stopped and the reaction mixture was cooled to room temperature and solidified. Reaction products were dissolved in chloroform and subjected to purification by using a silica gel column (eluting solvent: a chloroform-methanol mixed liquid) to give 47.5 g of the aimed compound 1 (yield: 67%).

white solid, melting point: 105° C.;

IR (cm$^{-1}$, ATR method): 3293, 2917, 2849, 1637, 1551, 1026;

$^1$H-NMR (CDCL$_3$, ppm): 0.85 (t, J=7 Hz, 3H), 1.10-1.38 (m, 24H), 1.90-2.01 (m, 2H), 2.07-2.26 (m, 1H), 2.26-2.40 (m, 2H), 2.40-2.58 (m, 1H), 2.64-2.77 (m, 1H), 3.05-3.20 (m, 2H), 3.44-3.66 (m, 4H), 3.66-3.75 (m, 2H), 5.23-5.35 (m, 1H), 5.40-5.53 (m, 1H), 6.74-6.90 (m, 2H).

Preparation Example 2: Synthesis of 2-(hexadecyl/octadecyl)-N,N,-bis(2-hydroxyethyl)succinamide (Compound 2)

(Compound 2)

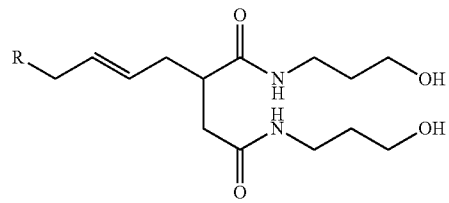

R=$C_{12}H_{25}$, $C_{14}H_{29}$

After Pd/C (0.3 g, 10%, Wako Pure Chemical Industries, Ltd.) was added to a solution of compound 1 (3.25 g, 7.42 mmol) in ethanol (150 ml) at room temperature under a nitrogen atmosphere, the atmosphere of the reaction system was changed to hydrogen. After one hour, crystals precipitated, and thus the reaction mixture was heated to 50° C., reacted for further 3 hours and then cooled to room temperature. After filtering to remove the Pd/C, the resultant reaction product was concentrated under reduced pressure to give 3.21 g of the aimed compound 2 (yield: 99%).

white solid, melting point: 122° C.;

IR (cm$^{-1}$, ATR method): 3285, 29182, 2849, 1647, 1552, 1063;

$^1$H-NMR (Pyridine-d$_5$, ppm): 0.84 (t, J=7 Hz, 3H), 1.05-1.35 (m, 28H), 1.38-1.48 (m, 1H), 1.48-1.58 (m, 1H), 1.58-1.68 (m, 1H), 1.90-2.00 (m, 1H), 2.64-2.75 (m, 1H), 3.00-3.11 (m, 1H), 3.25-3.35 (m, 1H), 3.64-3.88 (m, 4H), 3.94-4.12 (m, 4H), 8.90-9.01 (m, 1H), 9.01-9.10 (m, 1H).

Preparation Example 3: Synthesis of (E)-N,N,-bis(3-hydroxypropyl)-2-((hexadeca/octadeca)-2-en-1-yl)-succinamide (Compound 3)

(Compound 3)

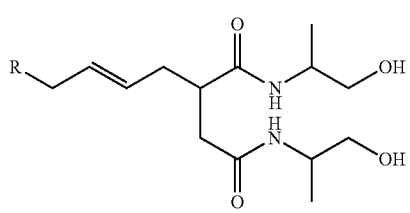

R=$C_{12}H_{25}$, $C_{14}H_{29}$

Similar to preparation example 1 except that propanolamine was used in place of ethanolamine, 44.1 g of the aimed compound 3 was synthesized (yield: 71%).

white solid, melting point: 97° C.;

IR (cm$^{-1}$, ATR method): 3298, 2919, 2851, 1645, 1546, 1049;

$^1$H-NMR (CDCL$_3$, ppm): 0.85 (t, J=7 Hz, 3H), 1.11-1.38 (m, 24H), 1.56-1.74 (m, 4H), 1.90-2.01 (m, 2H), 2.06-2.27 (m, 1H), 2.27-2.40 (m, 2H), 2.40-2.56 (m, 1H), 2.65-2.78 (m, 1H), 3.20-3.35 (m, 2H), 3.35-3.50 (m, 2H), 3.50-3.65 (m, 4H), 5.22-5.35 (m, 1H), 5.40-5.53 (m, 1H), 6.5 (bs, 2H).

Preparation Example 4: Synthesis of (E)-2-(hexadeca/octadeca)-2-en-1-yl)-N,N,-bis(1-hydroxypropan-2-yl)succinamide (Compound 4)

(Compound 4)

R=$C_{12}H_{25}$, $C_{14}H_{29}$

Similar to preparation example 1 except that DL-2-amino-1-propanol was used in place of ethanolamine, 35.8 g of the aimed compound 4 was synthesized (yield: 58%).

white solid, melting point: 105° C.;

IR (cm$^{-1}$, ATR method): 3286, 2918, 2850, 1644, 1544, 1042;

$^1$H-NMR (CDCL$_3$, ppm): 0.85 (t, J=7 Hz, 3H), 1.03-1.18 (m, 6H), 1.18-1.40 (m, 24H), 1.88-2.03 (m, 2H), 2.03-2.25 (m, 1H), 2.25-2.88 (m, 4H), 3.28-3.72 (m, 4H), 3.85-4.10 (m, 2H), 5.22-5.38 (m, 1H), 5.40-5.53 (m, 1H), 6.30-6.50 (m, 4H).

Preparation Example 5: Synthesis of (E)-2-(eicosa/docosa/tetracosa)-2-en-1-yl)-N,N,-bis(2-hydroxyethyl)succinamide (Compound 5)

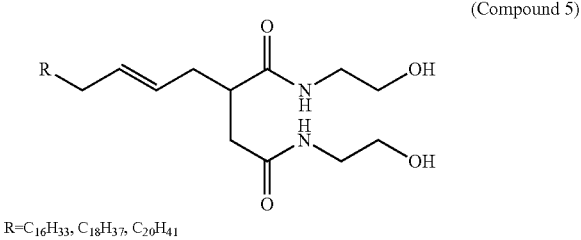

(Compound 5)

R=C$_{16}$H$_{33}$, C$_{18}$H$_{37}$, C$_{20}$H$_{41}$

<Production scheme>

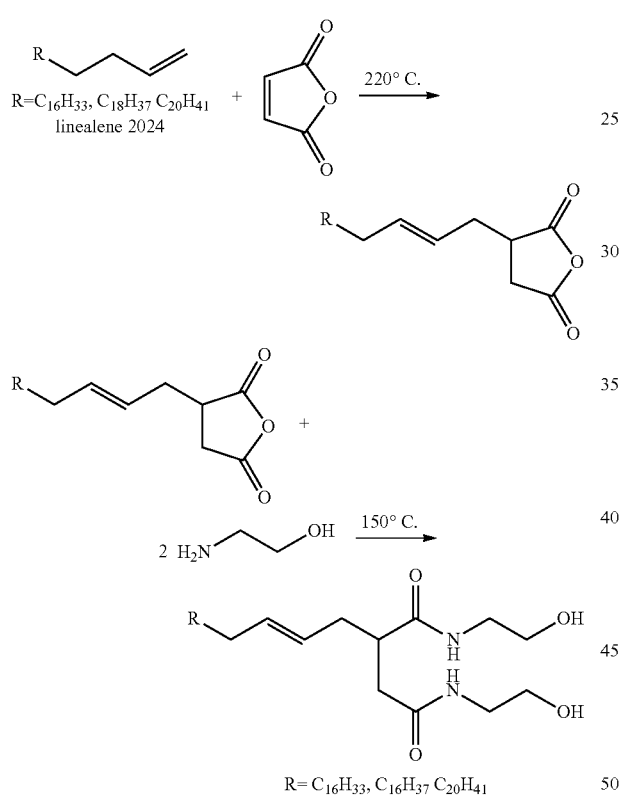

R= C$_{16}$H$_{33}$, C$_{16}$H$_{37}$ C$_{20}$H$_{41}$

Similar to preparation example 1 except that an alkenylsuccinic anhydride (mole ratio: C20/C22/C24=5/4/1, synthesized from maleic anhydride and linealene 2024 (IDEMITSU Kosan Co., Ltd.)) was used in place of the alkenylsuccinic anhydride (mole ratio: C16/C18=6/4), 42 g of the aimed compound 5 was synthesized (yield: 66%).

white solid, melting point: 130° C.;

IR (cm$^{-1}$, ATR method): 3283, 2917, 2849, 1636, 1552, 1052;

$^1$H-NMR (CDCL$_3$, ppm): 0.85 (t, J=7 Hz, 3H), 1.07-1.40 (m, 34H), 1.84-2.01 (m, 2H), 2.07-2.26 (m, 1H), 2.26-2.42 (m, 2H), 2.42-2.58 (m, 1H), 2.70-2.78 (m, 1H), 3.07-3.21 (m, 2H), 3.47-3.64 (m, 4H), 3.64-3.79 (m, 2H), 5.22-5.36 (m, 1H), 5.430-5.53 (m, 1H), 6.70-6.95 (m, 2H).

Preparation Example 6: Synthesis of (E)-N,N,-bis(1,3-dihydroxy-2-methylpropan-2-yl)-2-((hexadeca/octadeca)-2-en-1-yl)-succinamide (Compound 6)

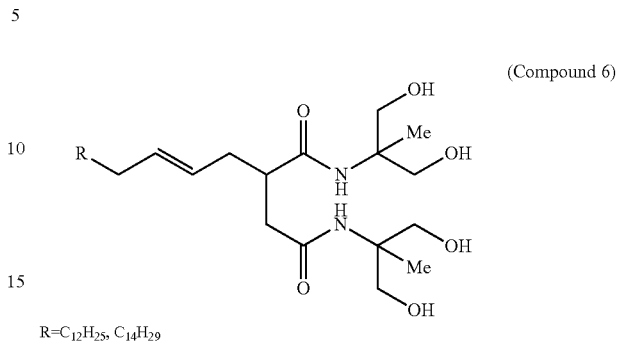

(Compound 6)

R=C$_{12}$H$_{25}$, C$_{14}$H$_{29}$

An alkenylsuccinic acid dimethyl ester (mole ratio: C16/C18=6/4, 15.0 g, 0.0392 mol), 2-amino-2-methyl-1,3-propanediol (8.25 g, 0.0785 mol) and 28% methanol solution of sodium methoxide (16.7 g, 0.0863 mol) were heated at 60° C. with stirring under a nitrogen atmosphere. After 10 hours, stirring was stopped and the reaction mixture was cooled to room temperature and solidified. Reaction products were dissolved in chloroform and subjected to purification using a silica gel column (eluting solvent: a chloroform-methanol mixed liquid) to give 8.46 g of the aimed compound 6 (yield: 51%).

pale yellow solid.

IR (cm$^{-1}$, ATR method): 3280, 2922, 2852, 1638, 1558, 1049;

$^1$H-NMR (CDCL$_3$, ppm): 0.85 (t, J=7 Hz, 3H), 1.15 (d, J=4 Hz, 6H), 1.20-1.40 (m, 24H), 1.91-2.02 (m, 2H), 2.10-2.27 (m, 1H), 2.27-2.56 (m, 3H), 2.60-2.72 (m, 1H), 3.50-3.66 (m, 4H), 3.66-3.79 (m, 2H), 3.79-3.97 (m, 2H), 5.23-5.35 (m, 1H), 5.43-5.57 (m, 1H), 6.32-6.50 (m, 2H).

Preparation Example 7: Synthesis of (E)-N,N,-bis(1,3-dihydroxy-2-(hydroxymethyl)propan-2-yl)-2-((hexadeca/octadeca)-2-en-1-yl)-succinamide (Compound 7)

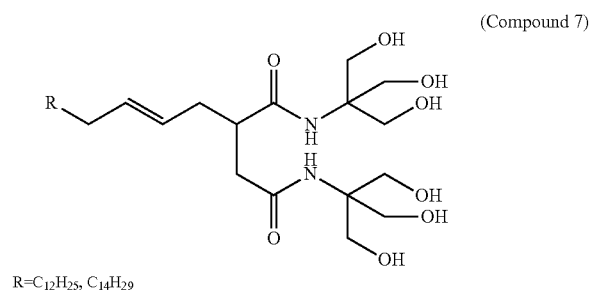

(Compound 7)

R=C$_{12}$H$_{25}$, C$_{14}$H$_{29}$

Similar to preparation example 6 except that tris(hydroxymethyl)aminomethane was used in place of 2-amino-2-methyl-1,3-propanediol, 5.73 g of the aimed compound 7 was synthesized (yield: 26%).

white solid, melting point: 62° C.;

IR (cm$^{-1}$, ATR method): 3313, 2919, 2851, 1647, 1548, 1045;

$^1$H-NMR (MeOH-d$_4$, ppm): 0.91 (t, J=7 Hz, 3H), 1.21-1.44 (m, 24H), 1.95-2.10 (m, 2H), 2.10-2.20 (m, 1H), 2.20-2.45 (m, 2H), 2.45-2.60 (m, 1H), 2.67-2.80 (m, 1H), 3.60-3.70 (m, 12H), 3.66-3.79 (m, 2H), 5.30-5.45 (m, 1H), 5.45-5.58 (m, 1H).

Reference Preparation Example 1: Synthesis of N-(2-hydroxyethyl)palmitamide (Comparative Compound 1)

(Comparative compound 1)

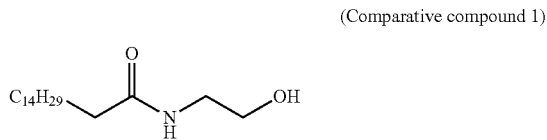

Isopropyl palmitate (300 g, 1.00 mol) and ethanolamine (82.0 g, 1.34 mol) were heated at 60° C. with stirring under a nitrogen atmosphere, and thereto were added 17.1 g of a sodium ethoxide/ethanol solution (20 wt %, 50.3 mmol) and methanol (100 ml). Four hours later, disappearance of the raw material ester was confirmed by TLC analysis, and then methanol (500 ml) was added thereto and the reaction mixture was cooled to room temperature to allow crystallization. The resultant crystals were filtered off and washed with methanol to give 268 g of the aimed comparative compound 1 (yield: 89%).

white solid, melting point: 100° C.;

IR (cm$^{-1}$, ATR method): 3293, 2917, 2849, 1638, 1552, 1056;

$^1$H-NMR (CDCL$_3$, ppm): 0.85 (t, J=7 Hz, 3H), 1.16-1.37 (m, 24H), 1.57-1.66 (m, 2H), 2.19 (t, J=8 Hz, 2H), 3.41 (q, J=5 Hz, 2H), 3.71 (t, J=5 Hz, 2H), 6.05 (bs, 1H).

Reference Preparation Example 2: Synthesis of (E)-2-(hexadeca/octadeca)-2-en-1-yl)-N,N,-bis(2-(2-hydroxy-ethoxy)ethyl)succinamide (Comparative Compound 2)

(Comparative compound 2)

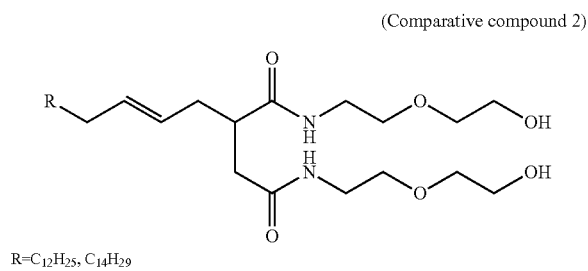

R=C$_{12}$H$_{25}$, C$_{14}$H$_{29}$

Similar to preparation example 1 except that diglycolamine was used in place of ethanolamine, 35.8 g of the aimed comparative compound 2 was synthesized (yield: 58%).

white solid, melting point: 57° C.;

IR (cm$^{-1}$, ATR method): 3284, 2919, 2851, 1651, 1552, 1068;

$^1$H-NMR (CDCL$_3$, ppm): 0.85 (t, J=7 Hz, 3H), 1.10-1.39 (m, 24H), 1.90-2.01 (m, 2H), 2.05-2.27 (m, 1H), 2.27-2.39 (m, 2H), 2.39-2.52 (m, 1H), 2.60-2.70 (m, 1H), 3.14-3.40 (m, 2H), 3.40-3.64 (m, 12H), 3.64-3.84 (m, 2H), 5.20-5.35 (m, 1H), 5.40-5.50 (m, 1H), 6.77 (bs, 1H), 6.87 (bs, 1H).

Reference Preparation Example 3: Synthesis of (E)-2-(hexadeca-2-en-1-yl)-N,N,-dihexadecylsuccinamide (Comparative Compound 3)

(Comparative compound 3)

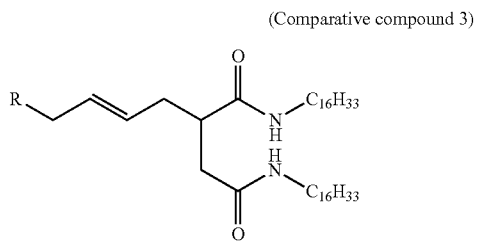

Similar to preparation example 1 except that hexadecylamine was used in place of ethanolamine, 35.8 g of the aimed comparative compound 3 was synthesized (yield: 58%).

white solid, melting point: 100° C.;

IR (cm$^{-1}$, ATR method): 3291, 2916, 2849, 1633, 1551;

$^1$H-NMR (CDCL$_3$, ppm): 0.85 (t, J=7 Hz, 9H), 1.08-1.39 (m, 80H), 1.90-2.01 (m, 2H), 2.05-2.23 (m, 1H), 2.23-2.37 (m, 2H), 2.37-2.48 (m, 1H), 2.54-2.65 (m, 1H), 3.07-3.26 (m, 4H), 5.23-5.35 (m, 1H), 5.40-5.50 (m, 1H), 5.79 (bs, 1H), 5.88 (bs, 1H).

Reference Preparation Example 4: Synthesis of (E)-2-(hexadeca/octadeca)-2-en-1-yl)-N-hexadecyl-N-(2-hydroxyethyl)succinamide (Comparative Compound 4)

(Comparative compound 4)

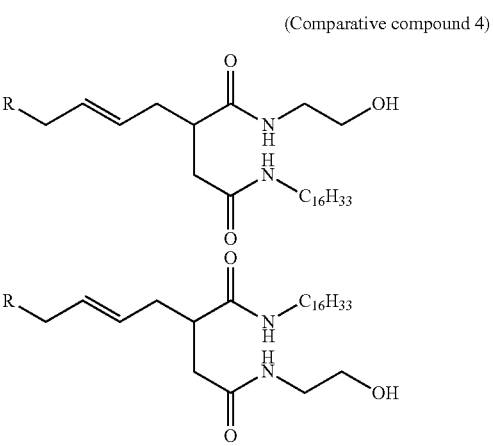

R=C$_{12}$H$_{25}$, C$_{14}$H$_{29}$

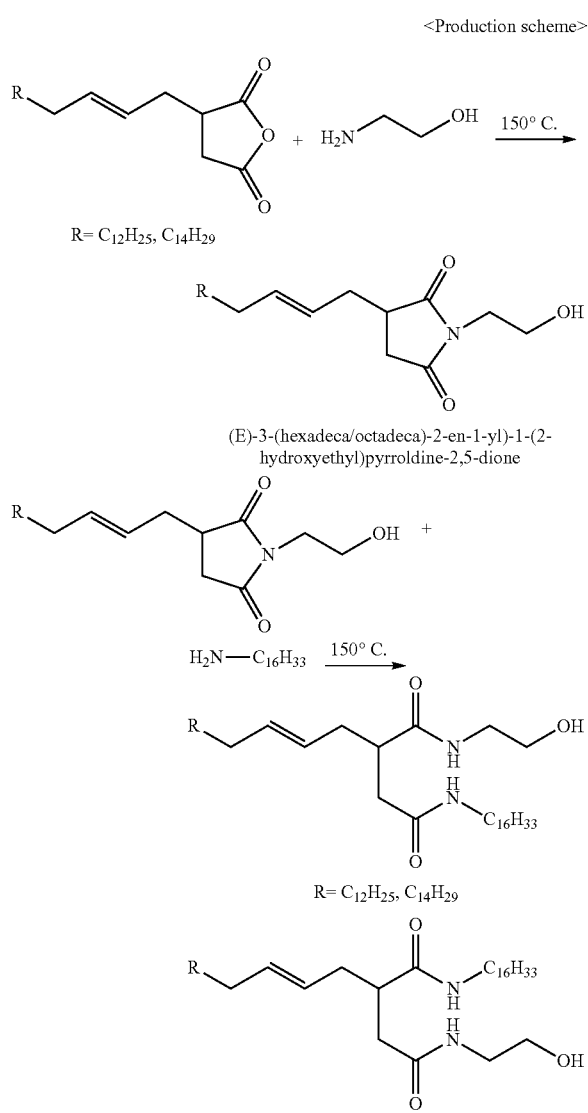

<Production scheme>

R= C$_{12}$H$_{25}$, C$_{14}$H$_{29}$ (E)-3-(hexadeca/octadeca)-2-en-1-yl)-1-(2-hydroxyethyl)pyrroldine-2,5-dione

R= C$_{12}$H$_{25}$, C$_{14}$H$_{29}$

Similar to preparation example 1 except that (E)-3-(hexadeca/octadeca)-2-en-1-yl)-1-(2-hydroxyethyl)pyrrolidine-2,5-dione (synthesized from an alkenylsuccinic anhydride (mole ratio: C16/C18=6/4) and ethanolamine) was used in place of the alkenylsuccinic anhydride (mole ratio: C16/C18=6/4), 5.94 g of the aimed comparative compound 4 was synthesized (yield: 35%).

white solid, melting point: 130° C.;

IR (cm$^{-1}$, ATR method): 3288, 2917, 2850, 1634, 1548, 1055;

$^1$H-NMR (CDCL$_3$, ppm): 0.86 (t, J=7 Hz, 6H), 1.10-1.39 (m, 52H), 1.39-1.50 (m, 28H), 1.89-2.02 (m, 2H), 2.08-2.23 (m, 2H), 2.23-2.38 (m, 2H), 2.38-2.55 (m, 1H), 2.59-2.68 (m, 1H), 3.07-3.19 (m, 1H), 3.19-3.32 (m, 2H), 3.37-3.47 (m, 1H), 3.57-3.72 (m, 2H), 5.23-5.36 (m, 1H), 5.40-5.53 (m, 1H), 5.82 (bs, 1H), 6.37 (bs, 1H).

Example 1: Evaluation of Lamellar-Formation Ability (X-Ray Diffraction)

Evaluation of lamellar-formation ability was conducted according to the method by Mizushima et al. (Lipids, 30(4), 327-332 (1995)).

1) Preparation of Evaluation Sample

Each of stearic acid and cholesterol, used as representatives of fatty acids that are horny layer intercellular lipids, as well as a sample to be evaluated was weighed to give an equimolar mixture, and an ion-exchange water was added thereto in an amount of 30 wt % of the weight of the lipids. The mixture was heat-melted and then cooled to give an evaluation sample.

2) X-Ray Diffraction Apparatus

Wide-angle X-ray diffraction apparatus ((PANalytical) X' Pert MRD High Resolution X-ray Diffractometer)

Small-angle X-ray scattering apparatus ((NANO Viewer manufactured by RIGAKU Corporation), Small-angle X-ray scattering)

3) X-Ray Diffraction Measurement

In the case where the wide-angle X-ray diffraction apparatus was used, sampling for measurement was conducted by finely grinding a sample in an agate mortar and packing the sample in a measurement cell to give a flat surface. In the case of small-angle X-ray scattering apparatus, the sample was packed in a cell made of stainless steel having grid openings of approximately 4 mm in width and 2 mm in depth.

Conditions for wide-angle X-ray diffraction measurement: measurement cell: a cell for exclusive use made of stainless steel, applied voltage: 45 kV, applied current: 40 mA.

measured range: 2θ=3° to 45°, measurement speed: 2θ=1°/min.

Conditions for small-angle X-ray measurement: measurement cell: a sample that was packed in a stainless steel holder having grid openings was measured.

applied voltage: 40 mV, applied current: 30 mA, X-ray irradiation period: 30 minutes, measured at a camera length of from 450 to 650 mm using a detector with an imaging plate.

4) Criteria for Evaluating Presence or Absence of Lamellar Formation Ability

In a wide-angle X-ray diffraction measurement, a symbol A was assigned to a sample wherein diffraction peaks originating from crystals of stearic acid and cholesterol disappeared and only the peaks originating from a lamellar structure were observed near 2θ=22°, a symbol B was assigned to a sample wherein diffraction peaks originating from crystals of stearic acid and cholesterol remained but peaks originating approximately from a lamellar structure were observed, a symbol C was assigned to a sample wherein peaks originating from a lamellar structure were observed only partly, and a symbol D was assigned to a sample wherein no peaks originating from a lamellar structure were observed. In addition, in a small-angle X-ray measurement, a symbol E was assigned to a sample wherein diffraction peaks originating from a periodic structure of lamellar structure were observed, and a symbol F was assigned to a sample wherein no diffraction peaks were observed.

5) Results of Measurement

The results of the X-ray diffraction measurement of the evaluated samples are shown in Table 1.

TABLE 1

| Evaluated sample | Evaluation of X-ray diffraction measurement | |
|---|---|---|
| | wide-angle X-ray measurement | small-angle X-ray measurement |
| Compound 1 | B | E |
| Compound 2 | B | E |
| Compound 3 | C | E |
| Compound 4 | C | E |
| Compound 5 | A | E |
| Compound 6 | B | E |
| Compound 7 | A | E |
| Comparative Compound 1 | D | F |
| Comparative Compound 2 | D | F |
| Comparative Compound 3 | D | F |
| Sphingolipid E (manufactured by Kao Corporation) | A | E |
| Ceramide 2 (manufactured by SEDERMA) | A | E |

Compounds 1-7 could form a lamellar structure together with stearic acid and cholesterol that are horny layer intercellular lipids, similar to Sphingolipid E and Ceramide 2 could.

Example 2: Evaluation as to Occlusion (TEWL-Inhibition)

Evaluation as to occlusion was conducted according to the method by Akasaki et al. (Fragrance Journal, extra edition, No. 13, p. 65, 1994).
1) Evaluation Method
Each of stearic acid and cholesterol, used as representatives of fatty acids that are horny layer intercellular lipids, and a sample to be evaluated was weighed into a screw tube, and a mixed liquid of chloroform and methanol (9:1 by volume) was used to give a 10% solution of the lipid mixture (w/v). A filter paper (ADVANTEC Co. Ltd., No. 5C, φ=21 mm) was immersed in the 10% solution, and then taken out, dried at room temperature, heated at 90° C. for one hour, hydrated by a water sprayer, heat-treated at 60° C. for 12 hours, and then cooled. The filter thus prepared was set in a vial charged with ion-exchange water (20 ml), and the weight of the filter was measured over time to calculate an amount of TEWL. As a control, was measured an amount of TEWL of a filter which had been immersed only in a mixed liquid of chloroform and methanol (9:1 by volume). A control rate of TEWL (%) was calculated according to the following equation:

Control rate of TEWL (%)=(1−amount of TEWL of evaluated sample/amount of TEWL of control)×100.

2) Results
A inhibition rate of TEWL of each evaluated sample (%, an average of the results of three time measurements) is shown in Table 2. Compounds 1-7 exhibited a TEWL inhibiting effect comparable to that of sphingolipid E and Ceramide 2 which were reported to have a TEWL inhibiting effect.

TABLE 2

| Evaluated sample | TEWL inhibition rate (%) |
|---|---|
| Compound 1 | 29.8 |
| Compound 2 | 34.0 |
| Compound 3 | 39.3 |
| Compound 4 | 33.2 |
| Compound 5 | 43.2 |
| Compound 6 | 40.1 |
| Compound 7 | 37.0 |
| Comparative compound 2 | 24.2 |
| Comparative compound 4 | 27.4 |
| Sphingolipid E ( manufactured by Kao Corporation) | 32.8 |
| Ceramide 2 (manufactured by SEDERMA) | 35.7 |

Example 3: Measurement on Bonded Water Content (Differential Scan Calorimetric Analysis)

Measurement on bonded water content was conducted according to the method by Akasaki et al. (Fragrance Journal, extra edition, No. 13, pp. 66-67, 1994).
1) Differential scan calorimetric analyzer: (DSC6100 (SII Seiko Instruments Inc.)).
2) Evaluation method
A sample prepared by adding ion-exchange water to an equimolar mixture of stearic acid and cholesterol, both used as representatives of fatty acids that are a horny layer intercellular lipid, and a sample to be evaluated, was encapsulated in a cell, and the water content thereof was measured. The temperature of the sample was raised from −40° C. at a rate of 1° C./minute to obtain an enthalpy change accompanied by the temperature raise. A bonded water content was determined from the relation between a water content of a lipid mixture (an amount of moisture absorbed) and a change of peak of enthalpy (melting heat), and an enthalpy change was obtained from the point 0.
3) Results
A bonded water content (% by weight) of each of the evaluated sample is shown in Table 3. Compounds 1-2 exhibited a water retention effect comparable to that of sphingolipid E and Ceramide 2 which were reported to have a high water retention effect.

TABLE 3

| Evaluated sample | Bonded water content (% by mass) |
|---|---|
| Compound 1 | 10.6 |
| Compound 2 | 12.4 |
| Sphingolipid E (manufactured by Kao Corporation) | 7.1 |
| Ceramide 2 (manufactured by SEDERMA) | 6.0 |

Example 4: Test of Application to Irritated Skin Model (1) Method
Two sites of irritated skin models in the inner side of front arm of each of ten healthy males and females aged from 20 to 50 were deemed as subject sites, and to one of the two sites was applied once a preparation of the present invention shown in Table 4 and to the other sites was applied once a comparative preparation. After 3 hours, these sites were washed and compared with each other as to the state of bare skin.

The irritated skin models were prepared by mounting a glass cup to each of the two sites of the inner side of front arm, placing 10 ml of an acetone-ether mixture (1:1, v/v) in each of the glass cups, shaking the mixture for 30 minutes, placing 10 ml of distillation water in the cup immediately after discarding the solvent, followed by shaking for 10 minutes.

An amount of TEWL and a water content of stratum corneum of the subject sites each before the irritated skin-inducing treatment (A), immediately after the treatment (B) and 3 hours after application of tested preparation (C) were measured according to the following method, and a degree of restoration of irritated skin was evaluated.

TABLE 4

| Wt % | Preparation of the invention | Comparative preparation |
| --- | --- | --- |
| Compound 5 | 2.02 | — |
| Cholesterol | 1.58 | 1.58 |
| Behenic acid | 1.40 | 1.40 |
| AMiSOFT HA-P | 0.32 | 0.32 |
| Arginine | 0.18 | 0.18 |
| 86% Glycerine | 9.30 | 9.30 |
| Purified water | 85.20 | 87.22 |
| Total | 100.00 | 100.00 |

(2) Measurement of Water Content of Stratum Corneum

After washing a site to be measured, the site was habituated for 20 minutes in an environment in which the temperature was set to 20° C. and the humidity was set to 40%. Using Corneometer CM825MP (Trade name, manufactured by Courage+Khazaka electronic GmbH), an average of 5 measured values per one site was deemed as a capacitance value of each subject site, and an average capacitance value of 10 panelists was calculated to evaluate a water content of stratum corneum. In addition, a capacitance restoration rate (%) was calculated as a rate of capacitance change $\Delta(B-C)$ caused by application of a tested preparation to irritated skin model, relative to a rate of capacitance change $\Delta(B-A)$ caused by the irritated skin-inducing treatment, whereby evaluating for each tested preparation improvement in water content of stratum corneum of irritated skin which had been decreased in water content of stratum corneum, and restoration effect. The results are shown in Table 5.

Capacitance restoration rate (%)=100×$\Delta(B-C)/\Delta(B-A)$.

(3) Measurement of Amount of Transepidermal Water Loss (TEWL)

After washing a site to be measured, the site was habituated under a condition set at 20° C. and a humidity of 40% for 20 minutes. Using Tewameter TM300MP (Trade name, manufactured by Courage+Khazaka electronic GmbH), a value measured once per one site was deemed as a TEWL value of each subject site, and an average TEWL value of 10 panelists was calculated to evaluate a barrier function. In addition, a barrier function-restoration rate (%) was calculated as a rate of TEWL change $\Delta(B-C)$ caused by application of a tested preparation to irritated skin model, relative to a rate of TEWL change $\Delta(B-A)$ caused by irritated skin-inducing treatment, whereby evaluating for each tested preparation improvement in barrier function of irritated skin and restoration effect. The results are shown in Table 6.

Barrier function-restoration rate (%)=100×$\Delta(B-C)/\Delta(B-A)$.

(4) Results

TABLE 5

Evaluation result of water content of stratum corneum average value ± SD (n = 10)

| | Capacitance value | | | |
| --- | --- | --- | --- | --- |
| | A Before irritated skin-inducing treatment | B Immediately after irritated skin-inducing treatment | C 3 hours after application | Capacitance restoration rate (%) |
| Present preparation | 36.1 ± 2.4 | 17.3 ± 2.0 | 25.3 ± 7.3 | 43.9 ± 38.8 |
| Comparative preparation | 36.2 ± 4.6 | 17.2 ± 3.9 | 21.6 ± 3.7 | 25.1 ± 15.2 |

TABLE 6

Evaluation result of barrier function average value ± SD (n = 10)

| | TEWL value | | | |
| --- | --- | --- | --- | --- |
| | A Before irritated skin-inducing treatment | B Immediately after irritated skin-inducing treatment | C 3 hours after application | barrier function-restoration rate (%) |
| Present preparation | 8.67 ± 2.25 | 12.03 ± 2.61 | 10.10 ± 2.21 | 65.5 ± 52.0 |
| Comparative Preparation | 8.66 ± 1.17 | 12.26 ± 2.17 | 11.08 ± 2.13 | 39.0 ± 42.8 |

As apparent from Table 5, comparing each of the capacitance values, no difference is recognized between the present preparation and the control preparation, both before the irritated skin-inducing treatment and immediately after the irritated skin-inducing treatment. However, the present preparation exhibited a higher value than that of the control preparation three hours after the application. With regard to capacitance restoration rate, the present preparation exhibited a higher rate than that of the control preparation. Namely, the results shown in Table 5 indicate that the compound of the present invention has the effects of improving the water content of horn cell layer and restoring the content thereof for irritated skin in which the water content of stratum corneum has decreased.

As apparent from Table 6, comparing each of the TEWL values, no difference is recognized between the present preparation and the control preparation both before the irritated skin-inducing treatment and immediately after the irritated skin-inducing treatment. However, after elapse of 3 hours after the application, the present preparation exhibited a significantly lower TEWL value than that of the control preparation (p<0.05). With regard to barrier function restoration rate, the present preparation exhibited a higher rate than that of the control preparation. Namely, the results shown in Table 6 indicate that the compound of the present invention has the effects of improving and restoring barrier function for irritated skin in which the barrier function thereof has decreased.

The invention claimed is:

1. A method for treating dry skin, irritated skin, atopic dermatitis, senile xerosis, and/or psoriasis, comprising administering an effective amount of a derivative of succinic acid diamide to a subject in need thereof,
wherein the derivative of succinic acid diamide is represented by formula (1):

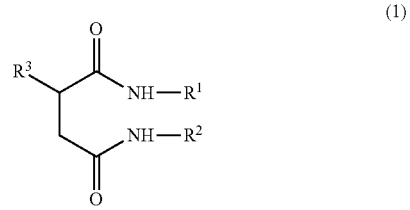

wherein
$R^1$ and $R^2$ each independently represents a hydroxyalkyl group of from 2 to 4 carbon atoms and from 1 to 3 hydroxyl groups, and
$R^3$ represents a group: —$CH_2CH_2CH_2CH_2$—$R^4$ or a group: —$CH_2CH$═$CHCH_2$—$R^4$, with $R^4$ representing an alkyl group of 8 to 26 carbon atoms.

2. The method of claim 1, wherein said administering comprises reinforcing skin barrier function.

3. The method of claim 1, wherein said administering comprises moisturizing skin.

4. The method according to claim 1, wherein $R^1$ and $R^2$ each independently is a monohydroxyalkyl group of from 2 to 4 carbon atoms.

5. The method according to claim 1, wherein $R^1$ and $R^2$ are independently selected from the group consisting of a 2-hydroxyethyl group; a 3-hydroxypropyl group; a 1-hydroxypropan-2-yl group; a 4-hydroxybutyl group; a 1,3-dihydroxy-2-methylpropan-2-yl group; a 1,3-dihydroxy-2-(hydroxymethyl)propan-2-yl group; a 1,2-dihydroxypropan-3-yl group; and a 1-hydroxy-2-(hydroxymethyl)propan-3-yl group.

6. The method according to claim 1, wherein $R^4$ represents an alkyl group of from 12 to 26 carbon atoms.

7. The method according to claim 1, wherein $R^4$ represents an alkyl group of from 16 to 20 carbon atoms.

8. The method according to claim 2, wherein $R^1$ and $R^2$ each independently is a monohydroxyalkyl group of from 2 to 4 carbon atoms.

9. The method according to claim 2, wherein $R^1$ and $R^2$ are independently selected from the group consisting of a 2-hydroxyethyl group; a 3-hydroxypropyl group; a 1-hydroxypropan-2-yl group; a 4-hydroxybutyl group; a 1,3-dihydroxy-2-methylpropan-2-yl group; a 1,3-dihydroxy-2-(hydroxymethyl)propan-2-yl group; a 1,2-dihydroxypropan-3-yl group; and a 1-hydroxy-2-(hydroxymethyl)propan-3-yl group.

10. The method according to claim 2, wherein $R^4$ represents an alkyl group of from 12 to 26 carbon atoms.

11. The method according to claim 2, wherein $R^4$ represents an alkyl group of from 16 to 20 carbon atoms.

12. The method according to claim 3, wherein $R^1$ and $R^2$ each independently is a monohydroxyalkyl group of from 2 to 4 carbon atoms.

13. The method according to claim 3, wherein $R^1$ and $R^2$ are independently selected from the group consisting of a 2-hydroxyethyl group; a 3-hydroxypropyl group; a 1-hydroxypropan-2-yl group; a 4-hydroxybutyl group; a 1,3-dihydroxy-2-methylpropan-2-yl group; a 1,3-dihydroxy-2-(hydroxymethyl)propan-2-yl group; a 1,2-dihydroxypropan-3-yl group; and a 1-hydroxy-2-(hydroxymethyl)propan-3-yl group.

14. The method according to claim 3, wherein $R^4$ represents an alkyl group of from 12 to 26 carbon atoms.

15. The method according to claim 3, wherein $R^4$ represents an alkyl group of from 16 to 20 carbon atoms.

16. The method according to claim 1, wherein said administering comprises applying an effective amount of the derivative of succinic acid diamide of the formula (1) to the human body for the purpose of reinforcing and returning to health of skin barrier functions or improvement in water-retention ability of skin.

17. The method according to claim 16, wherein said applying comprises contacting, directly or indirectly, a skin surface of a human body with the derivative of succinic acid diamide of the formula (1), to deliver an effective amount of the derivative of succinic acid diamide to at least one of the epidermis and dermis of the skin.

18. The method according to claim 16, wherein the effective amount of the derivative of succinic acid diamide of the formula (1) is from 0.01 to 5% by mass.

19. The method according to claim 17, wherein the effective amount of the derivative of succinic acid diamide of the formula (1) is from 0.01 to 5% by mass.

20. The method according to claim 2, wherein said administering comprises applying an effective amount of the derivative of succinic acid diamide of the formula (1) to the human body for the purpose of reinforcing and returning to health of skin barrier functions or improvement in water-retention ability of skin.

21. The method according to claim 20, wherein said applying comprises contacting, directly or indirectly, a skin surface of a human body with a derivative of succinic acid diamide of the formula (1), to deliver an effective amount of the derivative of succinic acid diamide to at least one of the epidermis and dermis of the skin.

22. The method according to claim 20, wherein the effective amount of the derivative of succinic acid diamide of the formula (1) is from 0.01 to 5% by mass.

23. The method according to claim 21, wherein the effective amount of the derivative of succinic acid diamide of the formula (1) is from 0.01 to 5% by mass.

24. The method according to claim 3, wherein said administering comprises applying an effective amount of the derivative of succinic acid diamide of the formula (1) to the human body for the purpose of reinforcing and returning to health of skin barrier functions or improvement in water-retention ability of skin.

25. The method according to claim 24, wherein said applying comprises contacting, directly or indirectly, a skin surface of a human body with a derivative of succinic acid diamide of the formula (1), to deliver an effective amount of the derivative of succinic acid diamide to at least one of the epidermis and dermis of the skin.

26. The method according to claim 24, wherein the effective amount of the derivative of succinic acid diamide of the formula (1) is from 0.01 to 5% by mass.

27. The method according to claim 25, wherein the effective amount of the derivative of succinic acid diamide of the formula (1) is from 0.01 to 5% by mass.

28. A method for treating atopic dermatitis, senile xerosis, and/or psoriasis, comprising administering an effective amount of a derivative of succinic acid diamide to a subject in need thereof,
wherein the derivative of succinic acid diamide is represented by formula (1):

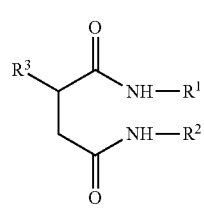 (1)
wherein
R$^1$ and R$^2$ each independently represents a hydroxyalkyl group of from 2 to 4 carbon atoms and from 1 to 3 hydroxyl groups, and
R$^3$ represents a group: —CH$_2$CH$_2$CH$_2$CH$_2$—R$^4$ or a group: —CH$_2$CH═CHCH$_2$—R$^4$, with R$^4$ representing an alkyl group of 8 to 26 carbon atoms.
* * * * *